US012667259B2

(12) United States Patent
Lai et al.

(10) Patent No.: US 12,667,259 B2
(45) Date of Patent: Jun. 30, 2026

(54) SYSTEM AND METHOD FOR TISSUE ANALYSIS USING REMOTE PPG

(71) Applicant: KONINKLIJKE PHILIPS N.V., Eindhoven (NL)

(72) Inventors: Marco Lai, Eindhoven (NL); Bernardus Hendrikus Wilhelmus Hendriks, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/837,733

(22) PCT Filed: Jan. 29, 2023

(86) PCT No.: PCT/EP2023/052103
§ 371 (c)(1),
(2) Date: Aug. 12, 2024

(87) PCT Pub. No.: WO2023/156173
PCT Pub. Date: Aug. 24, 2023

(65) Prior Publication Data
US 2025/0160653 A1 May 22, 2025

(30) Foreign Application Priority Data
Feb. 18, 2022 (EP) .................................... 22157397

(51) Int. Cl.
*A61B 5/00* (2006.01)
*A61B 5/0295* (2006.01)
*G06T 7/10* (2017.01)

(52) U.S. Cl.
CPC .......... *A61B 5/0082* (2013.01); *A61B 5/0295* (2013.01); *A61B 5/742* (2013.01);
(Continued)

(58) Field of Classification Search
CPC ................................................... G06T 7/0012
See application file for complete search history.

(56) References Cited

U.S. PATENT DOCUMENTS

2014/0275880 A1 9/2014 Verkruijsse
2017/0079530 A1 3/2017 Dimaio
(Continued)

FOREIGN PATENT DOCUMENTS

WO 2008085048 A1 7/2008
WO 2019003105 A1 1/2019

OTHER PUBLICATIONS

Sharma, Neeraj, and Lalit M. Aggarwal. "Automated medical image segmentation techniques." Journal of medical physics 35.1 (2010): 3-14.*

(Continued)

*Primary Examiner* — Carolyn A Pehlke

(57) ABSTRACT

A tissue analysis system and method process images to derive a remote PPG perfusion map from PPG amplitude levels obtained from the images as well as a PPG delay map from PPG relative delays between the PPG signals for each image region (pixel) with respect to a reference signal. The images are segmented into one or more tissue regions based on the PPG delay map (or segmentation information identifying tissue regions derived from the PPG delay map are received as input). The different tissue regions have distinct PPG delay characteristics. A level of perfusion can then be determined separately for each tissue region. Thus PPG delay information is used to enable different tissue types to be identified.

14 Claims, 10 Drawing Sheets

(52) U.S. Cl.
CPC ...... G06T 7/10 (2017.01); *G06T 2207/10004*
*(2013.01); G06T 2207/20084* (2013.01); *G06T*
*2207/30104* (2013.01)

(56) References Cited

U.S. PATENT DOCUMENTS

| | | | |
|---|---|---|---|
| 2017/0319114 A1 | 11/2017 | Kaestle | |
| 2017/0354334 A1* | 12/2017 | Tarassenko | A61B 5/742 |
| 2019/0175030 A1 | 6/2019 | Verkruijsse | |
| 2022/0354418 A1 | 11/2022 | Bourquin | |
| 2024/0041332 A1* | 2/2024 | Lokare | A61B 5/725 |
| 2024/0041342 A1 | 2/2024 | Lai | |

OTHER PUBLICATIONS

International Search Report and Written Opinion of PCT/EP2023/
052103, dated Mar. 9, 2023.
Zaunseder, Sebastian et al "Spatio-Tempoal Analysis of Blood
Perfusin by Imaging Photoplethysmography", Optical Diagnostics
and Sensing XVIII, Proc. of SPIE, vol. 10501, 2018.
Lai, Marco et al "Perfusion Monitoring by Contactless
Photoplethysmography Imaging", IEEE 16th International Sympo-
sium on Biomedical Imaging, Apr. 2019.
Lai, Marco et al "Evaluation of a Non-contact Photo-
Plethysmographic Imaging (iPPG) System for Peripheral Arterial
Disease Assessment", SPIE Medical Imaging, 2021.
Lai, Marco et al "Perfusion Monitoring by Non-Contact
Photoplethysmorgraphic (PPG) Imaging", R-TN-2016/00448, 2017.

* cited by examiner a)

b)

a)

b)

c)

120

122 Camera images

124 PPG Perfusion

126 PPG delay map

128 Segmentation

130 Perfusion Measure

SYSTEM AND METHOD FOR TISSUE ANALYSIS USING REMOTE PPG

CROSS-REFERENCE TO PRIOR APPLICATIONS

This application is the U.S. National Phase application under 35 U.S.C. § 371 of International Application No. PCT/EP2023/052103, filed on Jan. 29, 2023, which claims the benefit of European Patent Application No. 22157397.5, filed on Feb. 18, 2022. These applications are hereby incorporated by reference herein.

FIELD OF THE INVENTION

This invention relates to the analysis of tissue using photoplethysmography (PPG) analysis. The invention provides for a processors, systems including such processors, methods and computer programs for implementing the methods on e.g. such processors or systems.

BACKGROUND OF THE INVENTION

Microcirculation is the circulation of the blood in the smallest blood vessels, present in the vasculature embedded within organ tissues. The structure of the microvasculature is extremely complex, as so many capillaries are present in the tissues, with the individual capillaries so convoluted that the blood flow at any given point in any given capillary could be in any direction. For this reason, it can be stated that their overall function becomes averaged. That is, there is an average rate of blood flow through each tissue capillary bed, an average capillary pressure within the capillaries, and an average rate of transfer of substances between the blood of the capillaries and the surrounding interstitial fluid. This is the perfusion of the tissue.

Organ perfusion is a crucial indicator of injury and disease, which may include inflammation, stagnant or stopped blood flow, and all pathologies that can lead to global tissue hypoxia and organ dysfunction. Perfusion monitoring can be used to assess these microvascular injuries and many others, such as the progress of healing of either burned skin or wounds or the recovery of the perfusion downstream of a vessel lesion, and the necrosis (e.g., foot ulceration, sepsis) for patients with diabetes.

Non-contact PPG imaging is a recent emerging technology able of monitoring skin perfusion. PPG imaging utilizes an off-the-shelf camera and a light source to remotely detect the dynamic changes in blood volume beneath the skin and allows extracting blood pulsation signals. PPG imaging allows for the elaboration of large tissue areas, thus building a so-called perfusion map, which is a great advantage with respect to contact PPG. PPG imaging has shown to be capable of detecting skin perfusion perturbations, such as irritation, temperature changes and even flow blockage during pressure measurements and has even been evaluated for peripheral arterial disease assessment.

It is possible to build an amplitude map, that represents the amplitude of the PPG signal per image sensing pixel. Furthermore, it is also possible to build a delay map, which provides a measure of the average time delay between the PPG signal wave of each pixel and a reference PPG signal. There is a small delay in the blood pulsation arrival, due to small differences in the microcirculatory bad, such as the resistance and elasticity of the vessels, as well as different artery branches that supply the recorded tissues.

For the purposes of this application, which relates to processing of non-contact PPG signals, perfusion may be defined as the amplitude of a PPG signal of the tissue, namely the amplitude of the pulsatility extracted from the tissue.

It is well known that the perfusion level is not the same everywhere in the body. For example, in a study by the applicant, PPG imaging of the hands and feet were studied, and it was found that the perfusion level is higher on the palms of the hands rather than on the sole of the feet. This is also true for organs, such as the intestine. The small intestine and the colon have different functions, are far away and are supplied by different artery branches, and accordingly have different perfusion levels.

If different tissue types are present in a single image of a remote PPG camera, a general PPG image analysis will average these differences. For example, if an anastomosis is being performed (e.g. after removal of part of the intestine) and the level of perfusion is measured via PPG imaging, there are different intestines in the image. The image analysis will also not show whether the perfusion difference is physiological or due to a lesion (e.g. ischemia, inflammation).

For example, during open bowel resection, a part of the colon or small intestine is surgically removed to remove a tumor. First, a surgeon mobilizes the bowel from the surrounding organs and membranes. The bowel is clamped on both sides of the tumor and blood flow towards that part is interrupted. The surgeon will then cut out the diseased part of the bowel and stitch the two clamped sides back together, which is called the anastomosis. The intestinal anastomosis is to establish communication between two formerly distant portions of the intestine. This procedure restores intestinal continuity after removal of the pathological condition affecting the bowel. If the anastomosis does not properly heal due to inadequate perfusion, leakages occur. Leakages are dangerous and can lead to severe infections and require hospitalization and reoperation. These leakages occur in 5 to 10% of patients undergoing bowel resection. Here, objective perfusion parameters could help identify inadequate healing.

Zaunseder, Sebastian et. al., "Spatio-temporal analysis of blood perfusion by imaging photoplethysmography", Progress in Biomedical Optics and Imaging, SPIE-Int. Soc. for Optical Engineering vol. 10501, 20 Feb. 2018 (XP060099995) discloses a method of analyzing blood perfusion using remote PPG. A perfusion speed index is calculated for every pixel point of the PPG delay map. The distribution of all the indices give an indication on the perfusion.

US 2017/079530 discloses the use of optical imaging to provide tissue classification, in particular to distinguish between excised skin and burn tissue.

SUMMARY OF THE INVENTION

It would be desirable to be able to measure the perfusion separately in the two parts of the anastomosis, since the perfusion levels are not expected to be the same due to the anatomical differences between the different tissue types.

The invention is defined by the claims.

According to examples in accordance with an aspect of the current disclosure, there is provided a system for tissue analysis, comprising:

a processor adapted to receive images captured by an image sensor and to process the images to:

derive a PPG perfusion map from PPG amplitude levels obtained from the images;

derive a PPG delay map from PPG relative delays between different image regions;

segment the images into one or more tissue regions based on the PPG delay map or receive segmentation information identifying tissue regions derived from the PPG delay map, wherein the different tissue regions have distinct PPG delay characteristics; and determine a level of perfusion separately for each tissue region.

The system may be a medical system for internal and/or external body tissue analysis. The system may comprise or be an endoscope system. The system may be configured to observe or guide surgery. This system makes use of remote PPG sensing to derive a PPG perfusion map from PPG amplitude levels and a PPG delay map from relative delays of arrival of the pulsatile blood flow to the tissue. The delay information is for different image regions, i.e. the image data associated with different pixels of the image sensor.

The delay information enables different tissue types to be identified, either automatically or by user-selection after displaying a suitable representation of the PPG delay map. Different tissue regions for example have different general delay times.

It is then of interest to measure the perfusion in these portions separately as this gives a more accurate tissue assessment, as it takes account of the different tissue types and their possible different blood supplies.

The processor is for example adapted to segment the images based on regions with distinct ranges of PPG delay.

The PPG delay map is thus used for the classification of tissue types. For example, a first tissue region may have delay times in a first range which is non-overlapping with delay times in a second range of a second tissue type. Each range may be considered to be an average value plus or minus a number of standard deviations (i.e. a statistical range rather than a range which includes all values). Thus, they have distinct delay characteristics.

Thus, the tissue regions have distinct delay characteristics. This may arise because the different tissue types are supplied by different arteries and hence have a different path and hence path length to the heart. This may arise in the case of different portions of the intestines, and these portions may become adjacent during open bowel resection. There is a resulting intestinal anastomosis with communication between formerly distant portions of the intestine.

The relative delays for example comprise a delay relative to a reference PPG signal. The delay is computed as the average time delay between the PPG signal wave of each pixel and the reference PPG signal, over a certain time period.

The length of the time period includes at least a heartbeat cycle and the reference PPG signal is obtained as a spatial average of the all pixel values of a video (or series of images) which is a time-dependent signal modulated at the heart rate. A signal is created which varies over time, frame by frame.

The processor is for example adapted to segment the images using a machine learning algorithm.

The processor may be adapted to control a display to display the PPG perfusion map and the PPG delay map, and receive the segmentation information from a user to whom the PPG perfusion map and PPG delay map have been displayed.

Thus, the segmentation may be performed manually by a user of the system. It may instead be performed automatically by the system.

The processor is for example adapted to normalize the level of perfusion for each tissue region relative to a maximum level of perfusion within each tissue region. This enables variations in perfusion across an area to be more easily identifiable.

The relative delays for example comprise a delay relative to a reference PPG signal. The reference PPG signal in particular is an average PPG signal for the whole global region of interest hence including all of the tissue regions.

The tissue regions for example comprise tissue regions supplied by different arterial branches.

The system preferably further comprises an image sensor for capturing the images.

The current disclosure also provides a computer-implemented tissue analysis method, comprising:

receiving image sensor images;

deriving a PPG perfusion map from PPG amplitude levels obtained from the images;

deriving a PPG delay map from PPG relative delays between PPG signals of each image region with respect to a reference signal;

segmenting the images into one or more tissue regions based on the PPG delay map or receiving segmentation information identifying tissue regions derived from the PPG delay map, wherein the different tissue regions have distinct PPG delay characteristics; and determining a level of perfusion separately for each tissue region.

The image regions correspond to image sensor pixels.

The method may comprise segmenting the images based on regions with distinct ranges of PPG delay. The tissue regions for example comprise tissue regions supplied by different arterial branches. The images are for example segmented using a machine learning algorithm.

The method may comprise normalizing the level of perfusion for each tissue region relative to a maximum level of perfusion within each tissue region.

The relative delays for example comprise a delay relative to a reference PPG signal which is a spatial average of all the image regions in the image sensor image. The reference PPG signal is for example an average PPG signal for a global region of interest including all of the tissue regions or indeed all of the image regions (i.e. the whole captured image).

The current disclosure also provides a computer program comprising computer program code means which is adapted, when said program is run on a computer, to implement the method defined above. The current disclosure also provides a processor which is programed with the computer program.

These and other aspects of the current disclosure will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
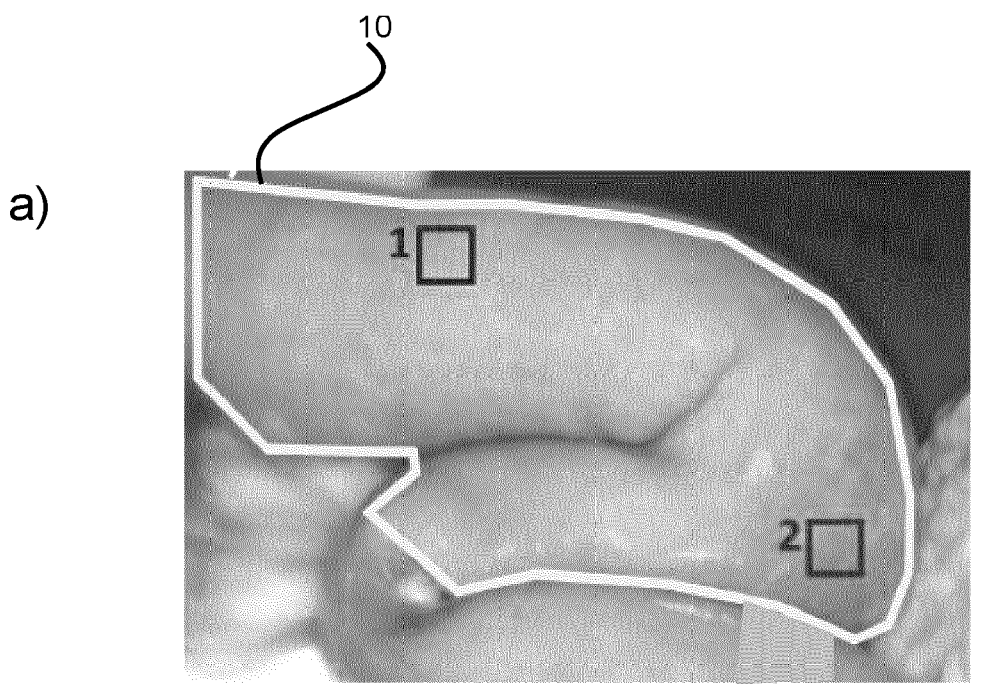
FIG. 1 shows a representation of a frame of a video acquired of the intestine and a global PPG signal derived from the video.
Figure 1:
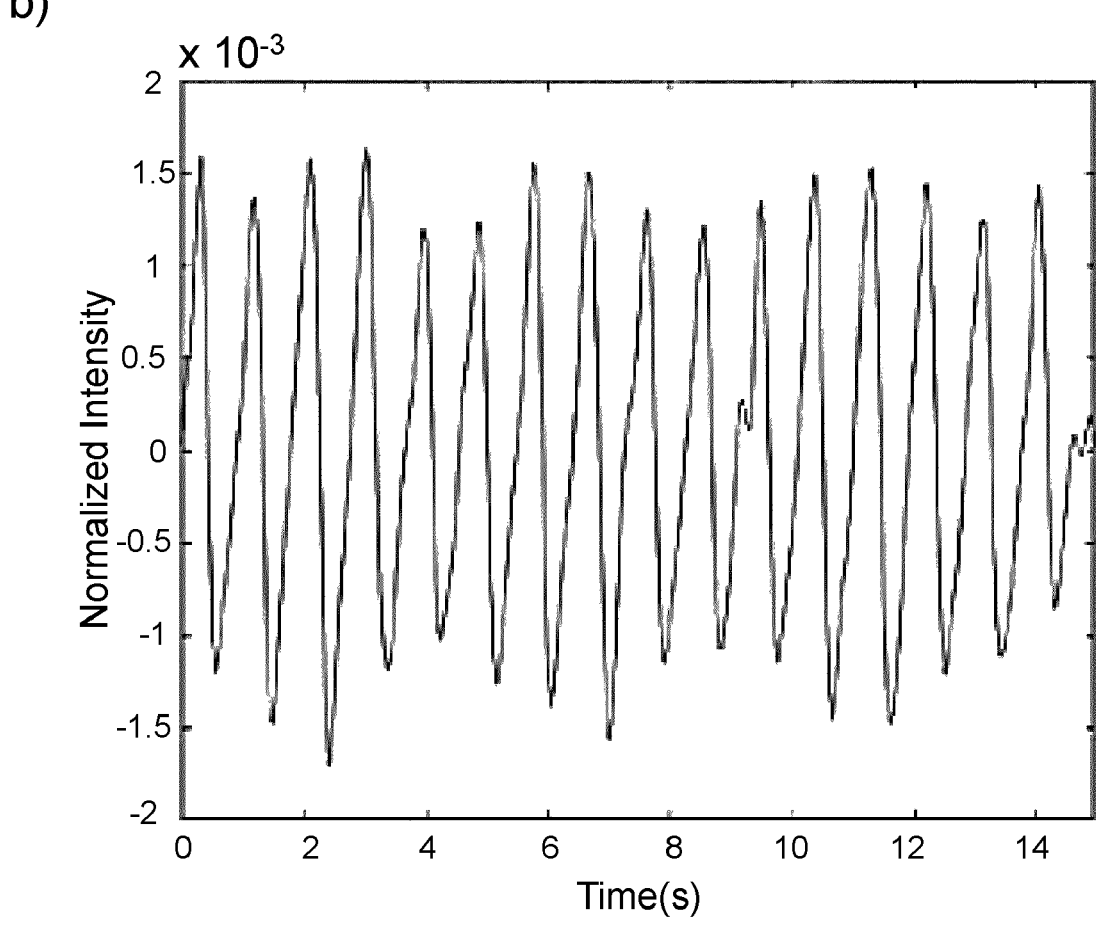

The invention will be described with reference to the Figures.

The detailed description and specific examples, while indicating exemplary embodiments of the apparatus, systems and methods, are intended for purposes of illustration only and are not intended to limit the scope of the claims. These and other features, aspects, and advantages of the apparatus, systems and methods of the present invention will become better understood from the following description, appended claims, and accompanying drawings. The Figures are merely schematic and are not drawn to scale. The same reference numerals are used throughout the Figures to indicate the same or similar parts.

The disclosure provides a tissue analysis system and method, which process images to derive a remote PPG perfusion map from PPG amplitude levels obtained from the images as well as a PPG delay map from PPG relative delays between the PPG signals for each image region (pixel) with respect to a reference signal. The images are segmented into one or more tissue regions based on the PPG delay map (or segmentation information identifying tissue regions derived from the PPG delay map is received as input). The different tissue regions have distinct PPG delay characteristics. A level of perfusion can then be determined separately for each tissue region. Thus PPG delay information is used to enable different tissue types to be identified.

Before describing the system and method of the invention, the known operation of a remote PPG imaging system, and the known image processing methods, will first be described.

Remote PPG imaging enables a determination of tissue perfusion from images captured of the tissue of interest, e.g. the skin or even tissue beneath the skin. Remote PPG typically uses ambient light, functioning as broad band white light source, and the diffuse and specular reflections are analyzed for different color components. Remote PPG imaging may be used to construct a PPG amplitude map and a PPG delay map.

For this purpose, a camera or a series of cameras (at one or multiple wavelengths) captures video of the tissue area, e.g. skin, at a distance. The measurements derived from the video are remote photoplethysmography (PPG) images, which provide non-contact measurement of a pulse signal by analyzing subtle changes of skin color (or organ color) i.e. at different wavelengths of the light.

It has been proposed to use remote PPG for inflammation detection. It has also been proposed in European Patent Application No. 20214955.5, which is incorporated by reference herein, to measure perfusion based both on a PPG amplitude level and also information about the distribution of the PPG phases, such as a standard deviation or inter-quartile range of a phase map.

By extracting pulse signals at each individual location of the skin region (corresponding to each pixel of the cameras) a spatial map of the pulse signal can be derived, showing both amplitude and delay. This perfusion map thus represents the amplitude and delay of the PPG signal per pixel and hence per location of the skin.

FIG. 1 (*a*) shows a representation of a frame of a video acquired of the intestine. By spatial averaging the pixel values in the region of interest (ROI) 10, a signal can be derived from the video, modulated at the heart rate. This signal is shown in FIG. 1 (*b*) as a normalized intensity of the PPG signal versus time.

The PPG signal of FIG. 1 (*b*) represents an average for the whole region of interest.

However, separate signals may also be captured from smaller regions of interest, shown as region 1 and region 2 in FIG. 1 (*a*).

Figures 2, 3:
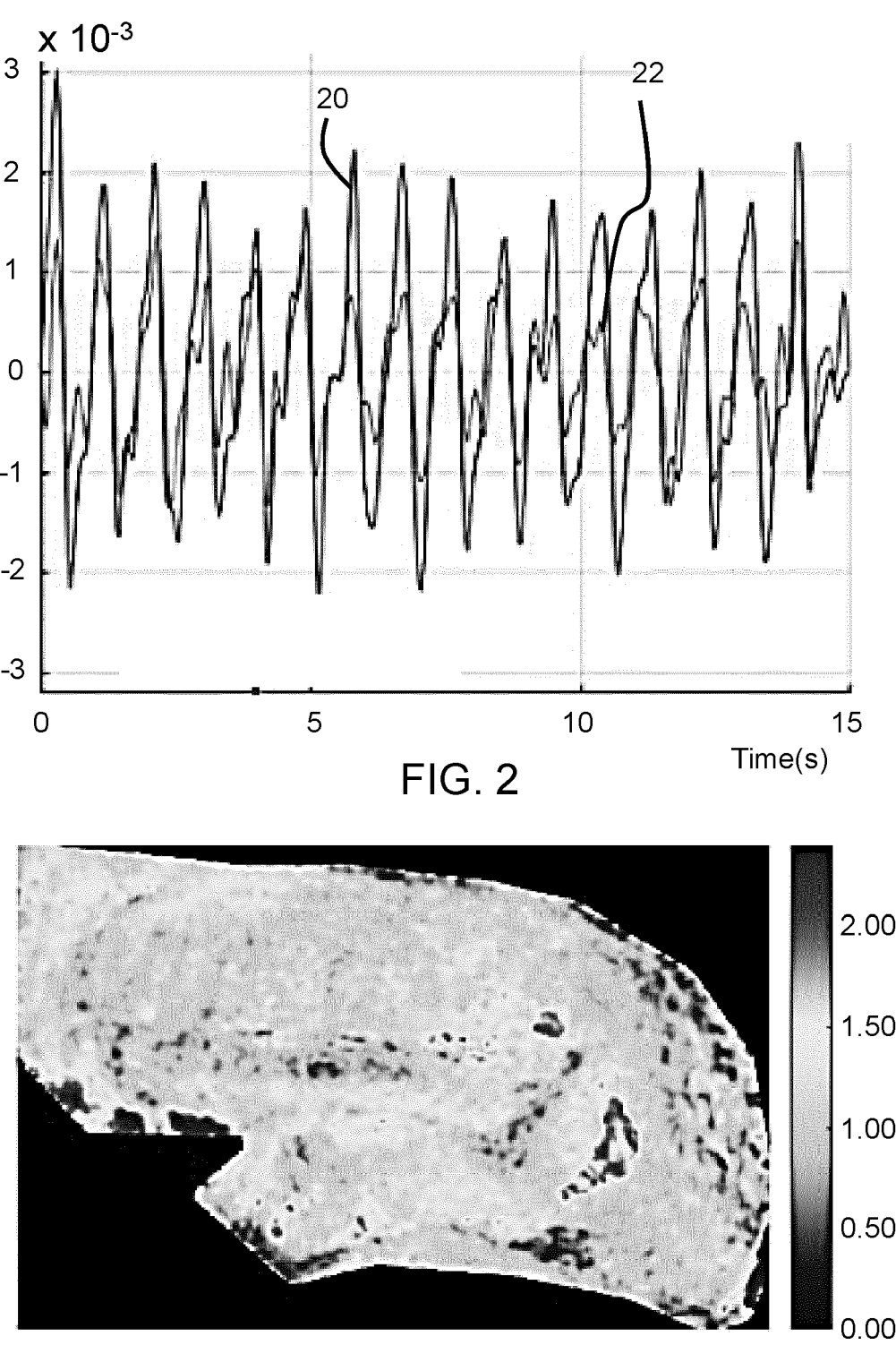
FIG. 2 shows separate PPG signals for separate regions of interest.
FIG. 3 shows a PPG perfusion map.

FIG. 2 shows separate PPG signals, as a first signal 20 for the first region of interest and a second signal 22 for the second region of interest. The two PPG signals are modulated at the same heart rate frequency, but show a different amplitude. By extracting the amplitude from the PPG signal of each separate region of tissue, i.e. from each corresponding pixel of the captured video, a PPG perfusion map may be obtained, as shown in FIG. 3.

FIG. 3 is a black and white representation. However, the PPG perfusion may be color-coded, for example assigning a more red color to areas with higher perfusion and a more blue color to areas with lower perfusion. The PPG amplitude map thus represents the amplitude of the PPG signal per pixel and hence per location of the skin or other tissue being analyzed.

Additional valuable information may be obtained by analyzing the PPG signals.

Figure 4:
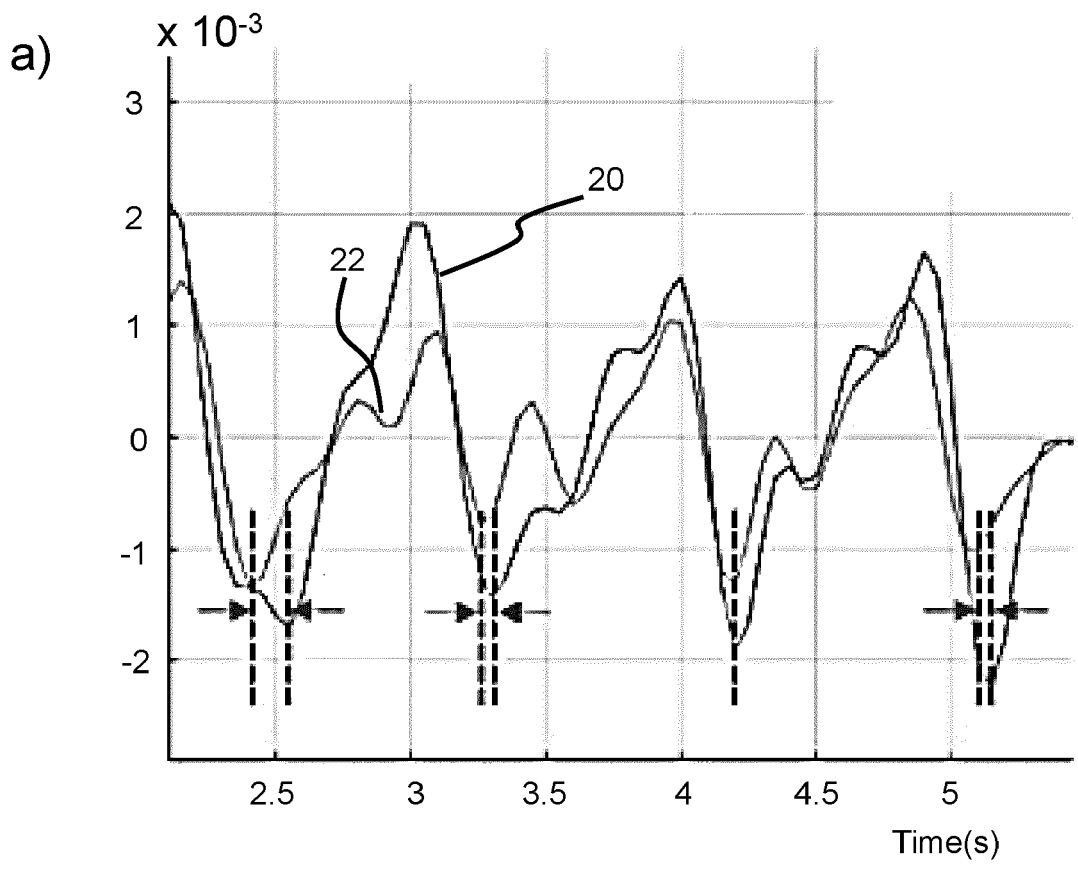
FIG. 4 shows a zoom-in of the PPG signals extracted from the two regions of interest from FIG. 2 and a PPG delay map.
Figure 4:
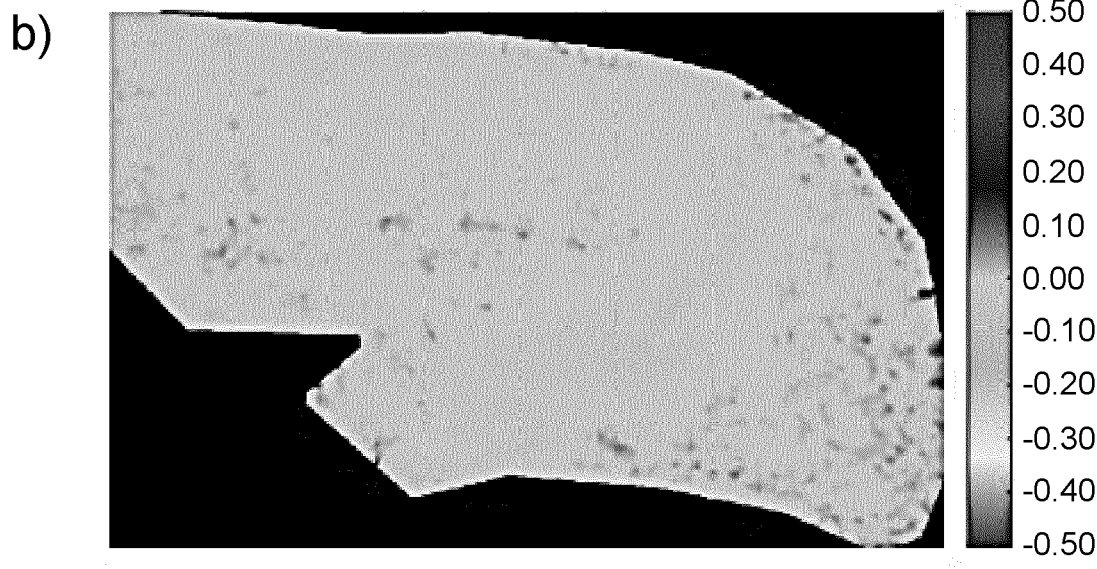

FIG. 4 (*a*) shows a zoom-in of the PPG signals extracted from the two regions of interest from FIG. 2. Even though the signals are extracted simultaneously from the same organ, the pulsation arrives slightly before in one area than in the other. There is a small delay in the blood pulsation arrival, due to small differences in the microcirculatory bed, such as the resistance and elasticity of the vessels, as well as different artery branches that supply the recorded tissues.

The delays of the PPG signals of each pixel with respect to a reference signal may be extracted and used for building a delay map. The delay map is shown in FIG. 4.

Since the delay between the signals is not always constant but varies during the acquisition, an average delay is used between signals per pixel.

The average delay represents the average time delay between the PPG signal of each pixel and a reference PPG signal. In this way a signal in time is built. The length of the PPG signal should include at least a heartbeat cycle, so it is subject dependent.

The average delay is a value of delay assigned to each pixel. From the plot of FIG. 4, it can be seen that there is a difference in time arrival between the peaks of the PPG signals. Therefore, for each pixel, the average of these delay (with respect to a reference signal) is assigned. At the end, the delay map is built, where each pixel contains the average delay between the PPG signal of that pixel and the reference PPG signal.

By acquiring a video stream, a series of images is obtained over time, for example with a frame rate of 20 frames per second. To compute the global PPG signal over time, the pixel values of the frame 1 are spatially averaged, so that the 2D set of pixels yields one value. The pixels of frame 2 are then averaged, and so on.

Eventually, a PPG signal is obtained over time (with the same length as the video that has been acquired), where each value of the signal is a spatial average of one corresponding frame of the video acquired. The image frames for example comprise 968×728 pixels, by way of example.

The PPG signal of each pixel is thus compared with the global PPG signal being used as a reference. The value assigned to each pixel "n" of the delay map thus represents the average delay between the PPG signal in the pixel "n" and the global PPG signal being used as a reference. Thus, the value of the delay for each pixel in the PPG delay map represents the average delay (in terms of average time shift) between the PPG signal of that pixel and the global PPG signal. The delays are for example computed by using the lock-in amplification algorithm.

The delay map thereby provides a measure of the average time delay between the PPG signal wave of each pixel and the reference PPG signal for at least one heartbeat cycle. The reference PPG signal is the global PPG signal of FIG. 1 (b) extracted from the entire region on interest of the intestine.

Since the reference signal is extracted from the entire region of interest, a PPG signal from a given location of the image is likely to be in phase with the reference.

Similar to the map of the amplitude, FIG. 4 (b) is a black and white representation. However, the PPG delay map may be color-coded. The Hue, Saturation, Value (HSV) color system is for example employed, since it works well with the periodicity of the PPG signal.

For extracting the amplitude maps and delay maps, a lock-in amplification method may be used.

Details on how to calculate the PPG maps using the lock-in amplification method can be found in, both of which are incorporated by reference herein:

(i) Lai M, Shan C, Ciuhu-Pijlman C, Izamis ML. Perfusion monitoring by contactless photoplethysmography imaging, 2019 IEEE 16th International Symposium on Biomedical Imaging (ISBI 2019) 2019 Apr. 8 (pp. 1778-1782). IEEE; and (ii) Lai M, Dicorato C S, de Wild M, Verbakel F, Shulepov S, Groen J, Notten M, Lucassen G, van Sambeek M R, Hendriks B H. Evaluation of a non-contact Photo-Plethysmographic Imaging (iPPG) system for peripheral arterial disease assessment, Medical Imaging 2021: Biomedical Applications in Molecular, Structural, and Functional Imaging 2021 Feb. 15 (Vol. 11600, p. 116000F). International Society for Optics and Photonics.

Because of the great advantages that the remote PPG technology has shown for remotely and non-invasively assessing skin-level perfusion, PPG imaging can be translated to organ perfusion assessment for detecting the perfusion of the microvasculature tissue bed beneath the organ surface, without any modification to the current acquisition setup.

FIG. 5(a) shows an image of an intestinal area after open bowl resection. FIG. 5(b) shows the corresponding amplitude map (normalized with respect to the maximum value) and FIG. 5(c) shows the corresponding delay map.

The delay map most clearly shows that there are two areas which each have a relatively uniform delay value but they are different to each other (in color, the two images are predominantly different colors, such as blue and green).

The areas are supplied by different arterial branches and there is a relative difference in the PPG time arrival between the areas. This can be assessed by comparing the PPG signals extracted from the two areas.

Figure 6:
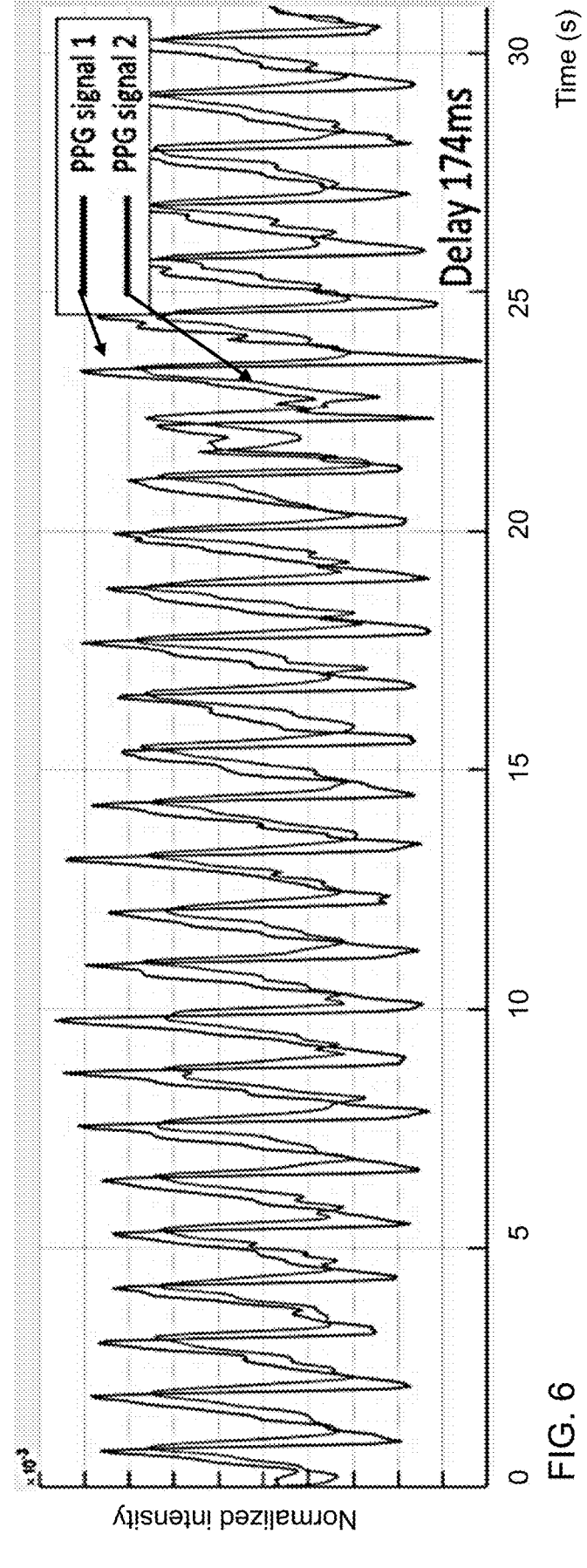
FIG. 6 shows an average PPG amplitude for each area.

FIG. 6 shows the average PPG amplitude for each area (with PPG signal 1 and PPG signal 2). The PPG amplitude level is different, but it can also be seen that one PPG signal arrives slightly before the other. The relative delay is 174 ms.

In the case of FIG. 1, the delay between different areas is relatively small and is mainly due to slight changes in vascular resistance and compliance. However, the delay seen in FIG. 6 is dependent on the PPG arrival time in the two areas.

The two areas will each have a spread of different delay times. However, each area will have a different average and an associated spread. Thus, ranges of PPG delay times, from the PPG delay map, may be used for classification.

For example, two areas of a PPG delay map may be considered separate if the difference of their delays is larger than a threshold such as 20 ms, preferably more than 50 ms and even more preferred larger than 100 ms.

The approach of the invention is explained with referenced to FIGS. 7 to 10.

Figure 5:
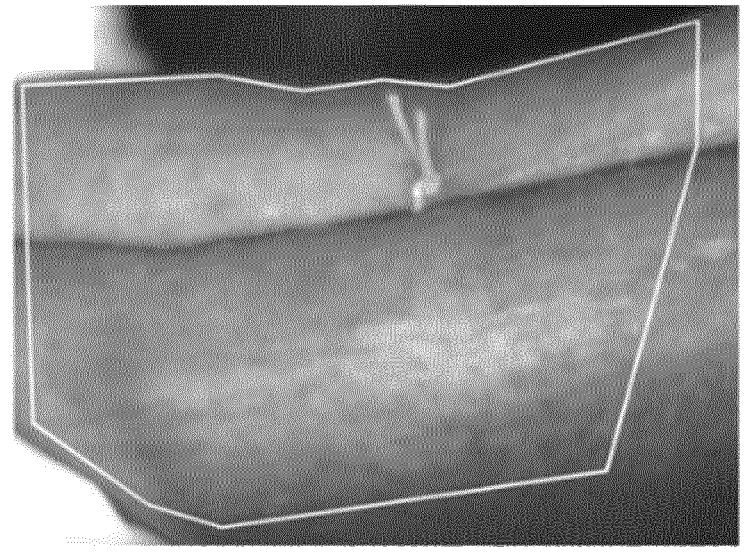
FIG. 5 shows an image of an intestinal area after open bowl resection, the corresponding amplitude map and the corresponding delay map.
Figure 5:
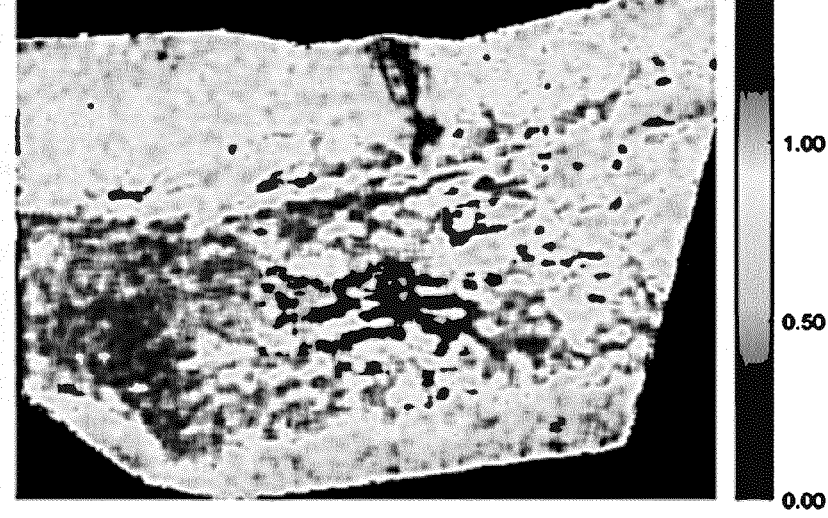
Figure 5:
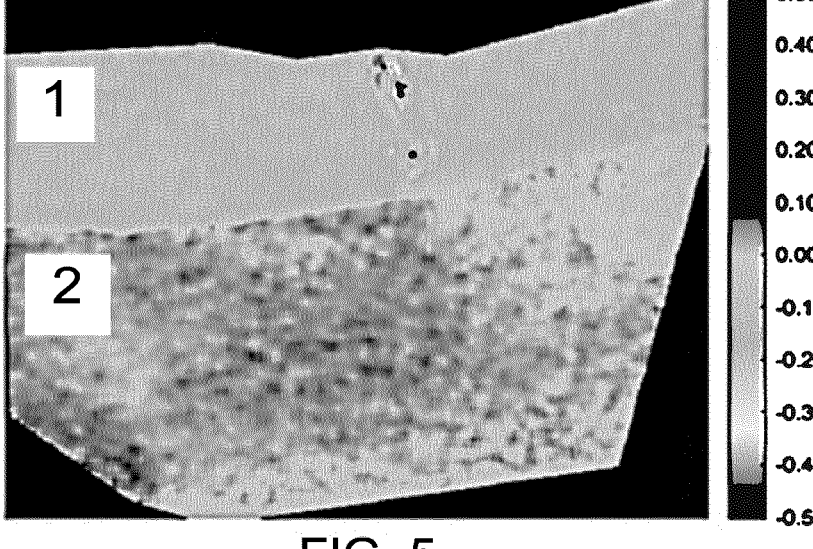
Figure 7:
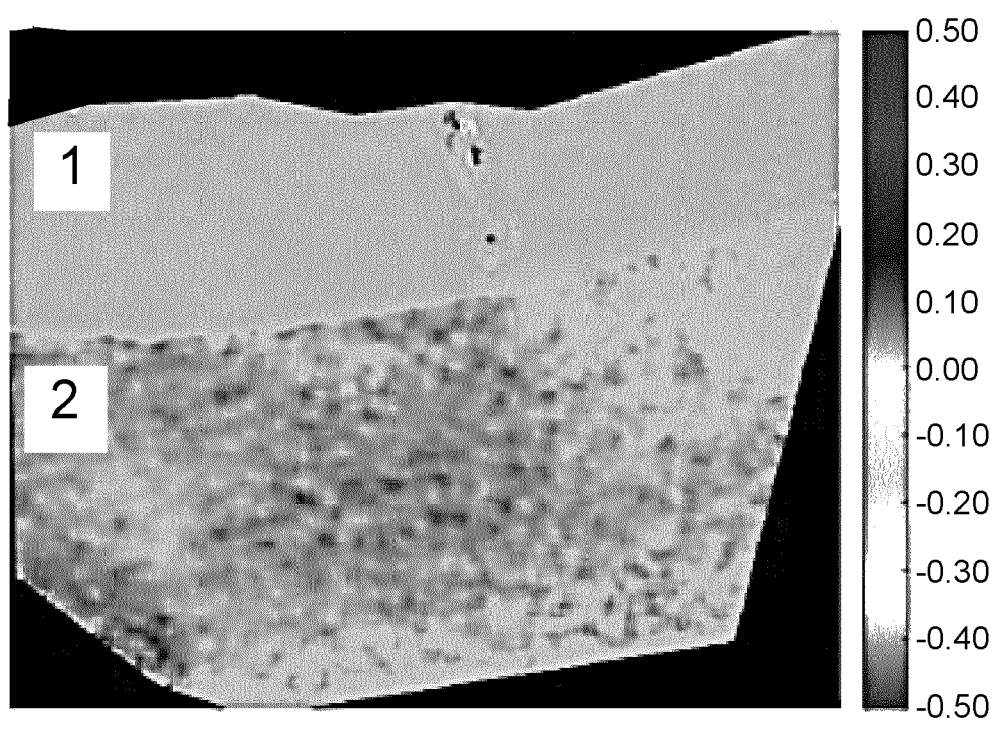
FIG. 7 shows the delay map for both areas.

FIG. 7 shows the delay map, corresponding to FIG. 5 (c).

The delay map is analyzed to identify uniform areas with different PPG delay arrival time, by identifying regions with distinct ranges of PPG delay as explained above. These regions have a delay relative to each other greater than a first threshold and also a spread of delays within the region below a second threshold. This spread of delays is for example a standard deviation or an interquartile range, or any other statistical measure of spread.

Figure 8:
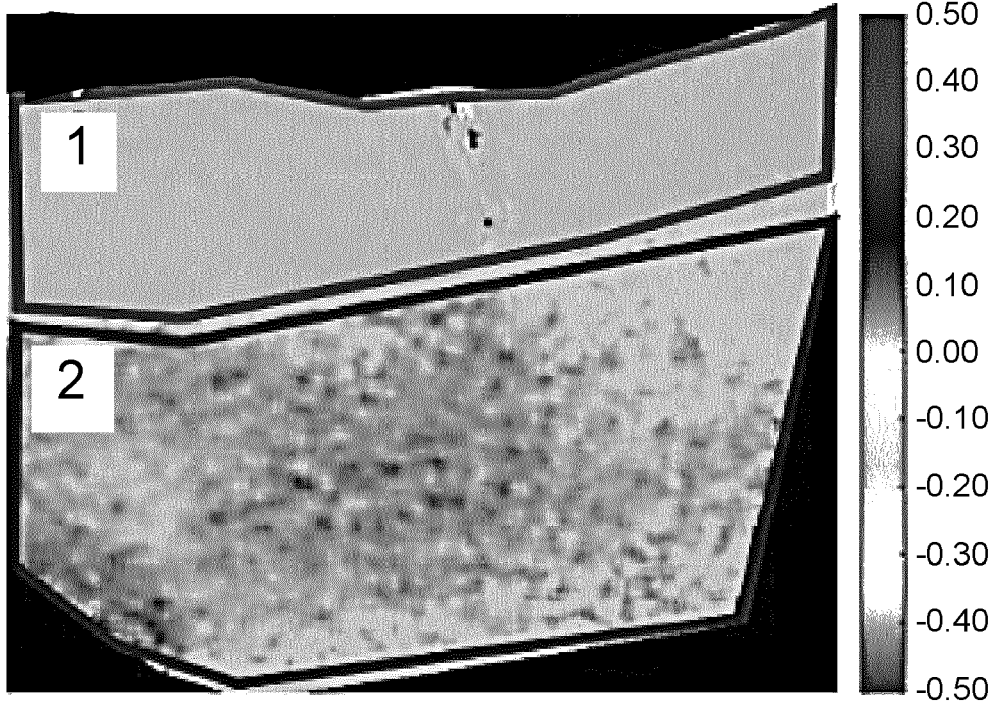
FIG. 8 shows a segmented version of the delay map.

This allows the field of view to be segmented into the different regions as shown in FIG. 8.

These areas of uniform but distinct delay could be identified by an operator by simply looking at the image and then providing an input to the system, or else an automatic or semi-automatic algorithm may be used for image classification (such as a computer vision algorithm or a deep learning algorithms).

Once the separate areas are identified on the delay map, the same areas are overlaid and selected on the PPG amplitude map.

The level of perfusion is then assessed within each selected amplitude map area, for example normalized with respect to their respective maxima.

Figure 9:
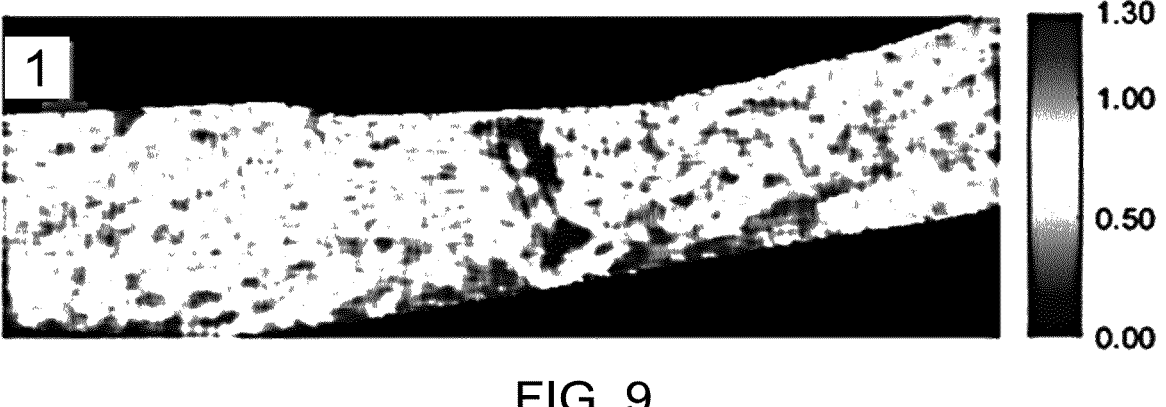
FIG. 9 shows the perfusion map for the first area.
Figure 10:
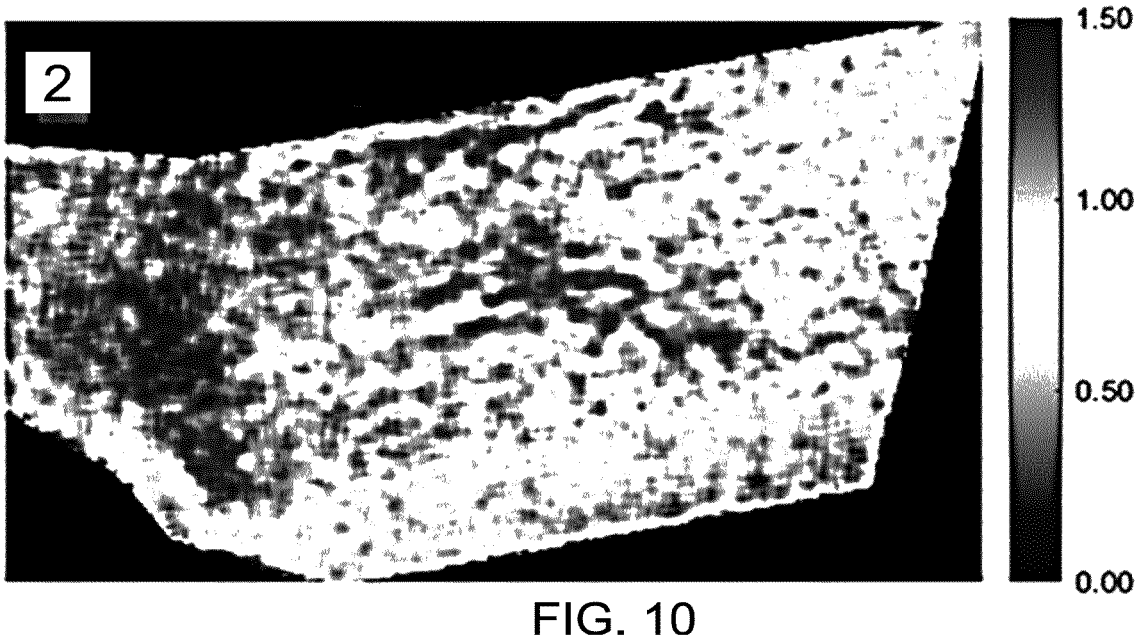
FIG. 10 shows the perfusion map for the second area.

FIG. 9 shows the perfusion map for the first area and FIG. 10 shows the perfusion map for the second area. Separate perfusion measurements may thus be provided for the different tissue areas. Thus, a global average perfusion measure is made for each segmented area.

The systems, methods and programs disclosed and claimed herein may be used for comparing or assessing the delay in PPG arrival time of organs supplied by different branches. For example, if the field of view of the camera is large enough, several organs could be imaged all at once. It could also be used for assessing the delay of PPG arrival outside the body, for example in videos where both hands and feet are recorded simultaneously in the same field of view. In oncological surgery, parts of the tissue containing tumor tissue have to be resected as explained above. Knowing which area is perfused by the same blood vessel is important for the resection i.e. where to cut for the resection especially when also blood vessel have to resected when embedded in the tumor.

Figure 11:
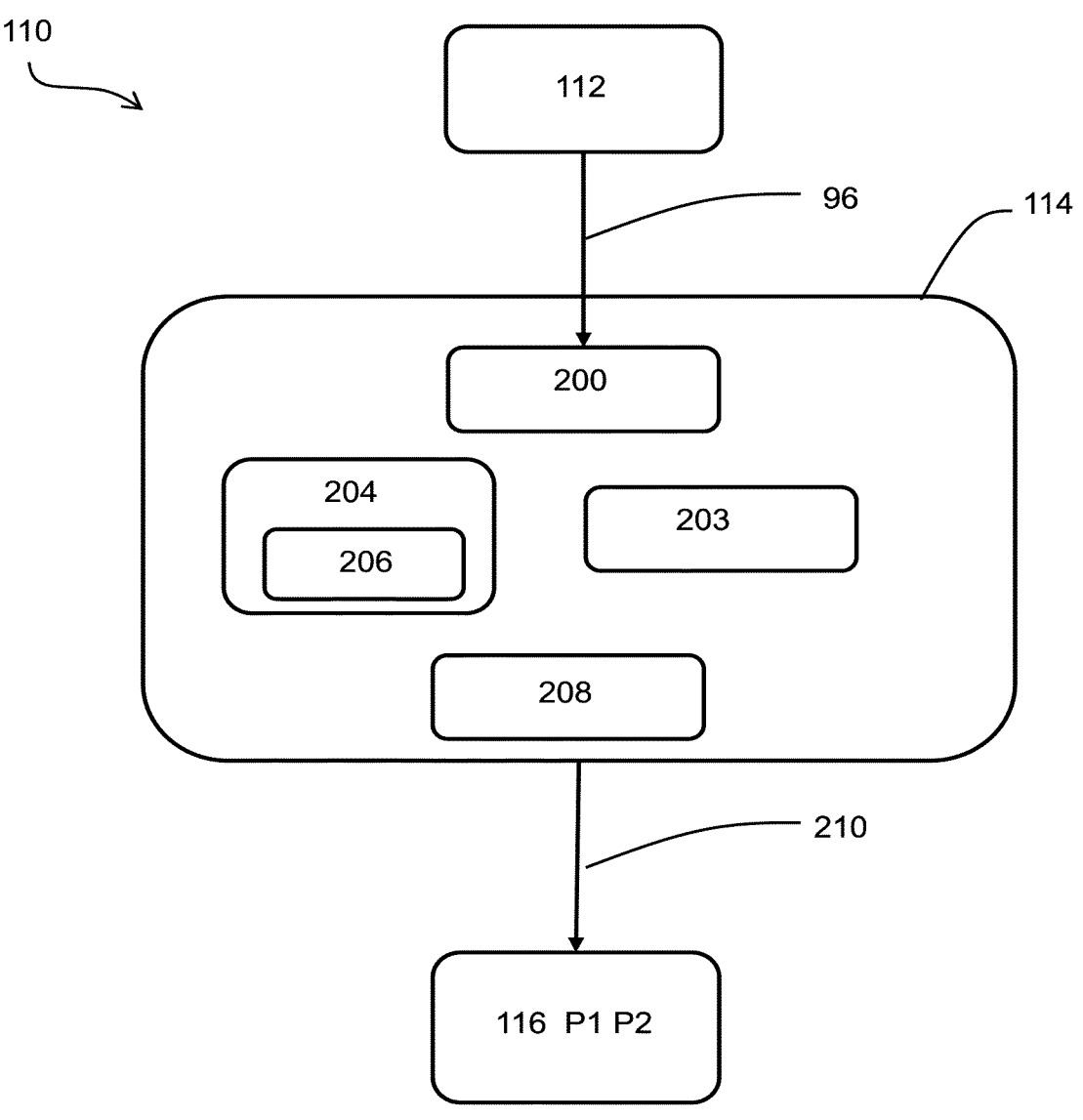
FIG. 11 shows system for tissue analysis.

FIG. 11 shows system 110 for tissue analysis. The system comprises one or more imaging cameras 112 and/or image repositories 112 and a processor 114 adapted to receive the images and process the images 96.

The image processing segments the tissue into different regions as explained above and perfusion measures P1, P2, based on average PPG amplitude levels for the segmented areas, are obtained for each tissue area from a PPG perfusion map.

The system has a display 116 for displaying the output, for example as a perfusion map and a delay map and/or as PPG signals over time.

The tissue classification may use machine learning algorithms, such as Support Vector Machines (SVMs) and Convolutional Neural Networks (CNNs).

The field of view of the camera could include all of the organs inside the abdomen or only a part of the organs inside. By classifying the tissue types present in the field of view, a comparison of perfusion is prevented between tissue which can have different levels of perfusion due to their different functions and they can even be supplied by different artery branches.

Figure 12:
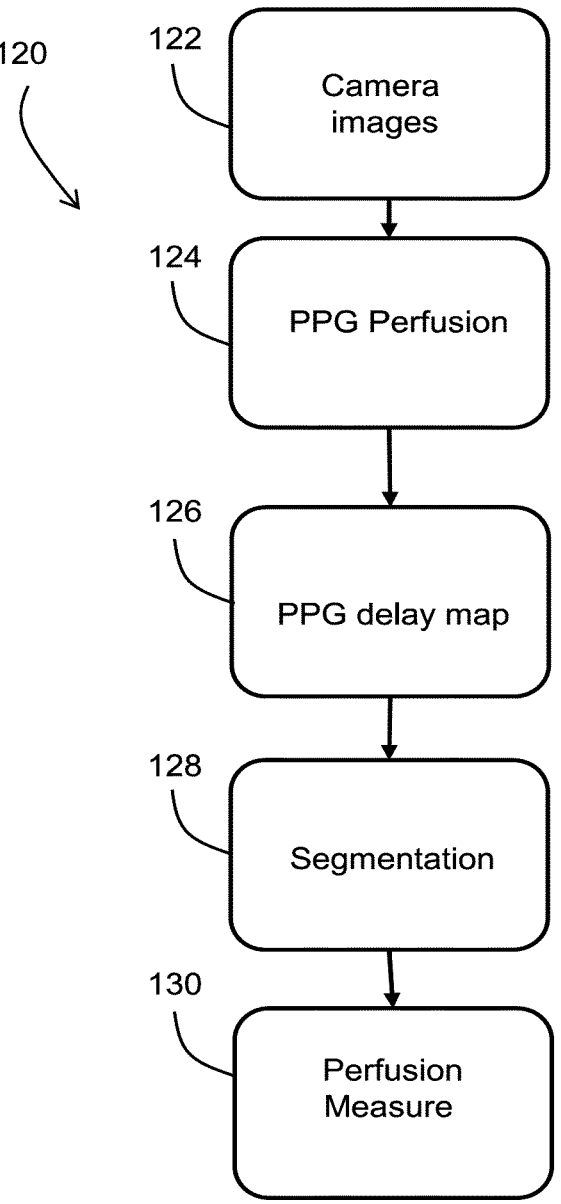
FIG. 12 shows a method for tissue analysis.

FIG. 12 shows a computer-implemented tissue analysis method 120. The method 120 comprises receiving image sensor images in step 122.

A PPG perfusion map is obtained from PPG amplitude levels obtained from the images in step 124;

In step 126, a PPG delay map is derived from PPG relative delays between different image regions.

Images are then segmented in step 128 into one or more tissue regions based on the PPG delay map (or after receiving segmentation information identifying tissue regions derived from the PPG delay map). The different tissue regions have distinct PPG delay characteristics.

A level of perfusion is then determined separately for each tissue region.

In FIG. 12, the PPG perfusion and PPG delay map are shown sequentially, but in practice the processing is preferably performed simultaneously.

The remote PPG sensing used in the system and method described above may be performed using broad band illumination, such as using ambient light and visible light cameras.

However, there is also the option of using hyperspectral imaging. Hyperspectral imaging (HSI) is an emerging imaging modality for medical applications that offers great potential for non-invasive disease diagnosis and surgical guidance. The objective of hyperspectral imaging is to collect a three-dimensional dataset of spatial and spectral information, known as hypercube.

Figure 13:
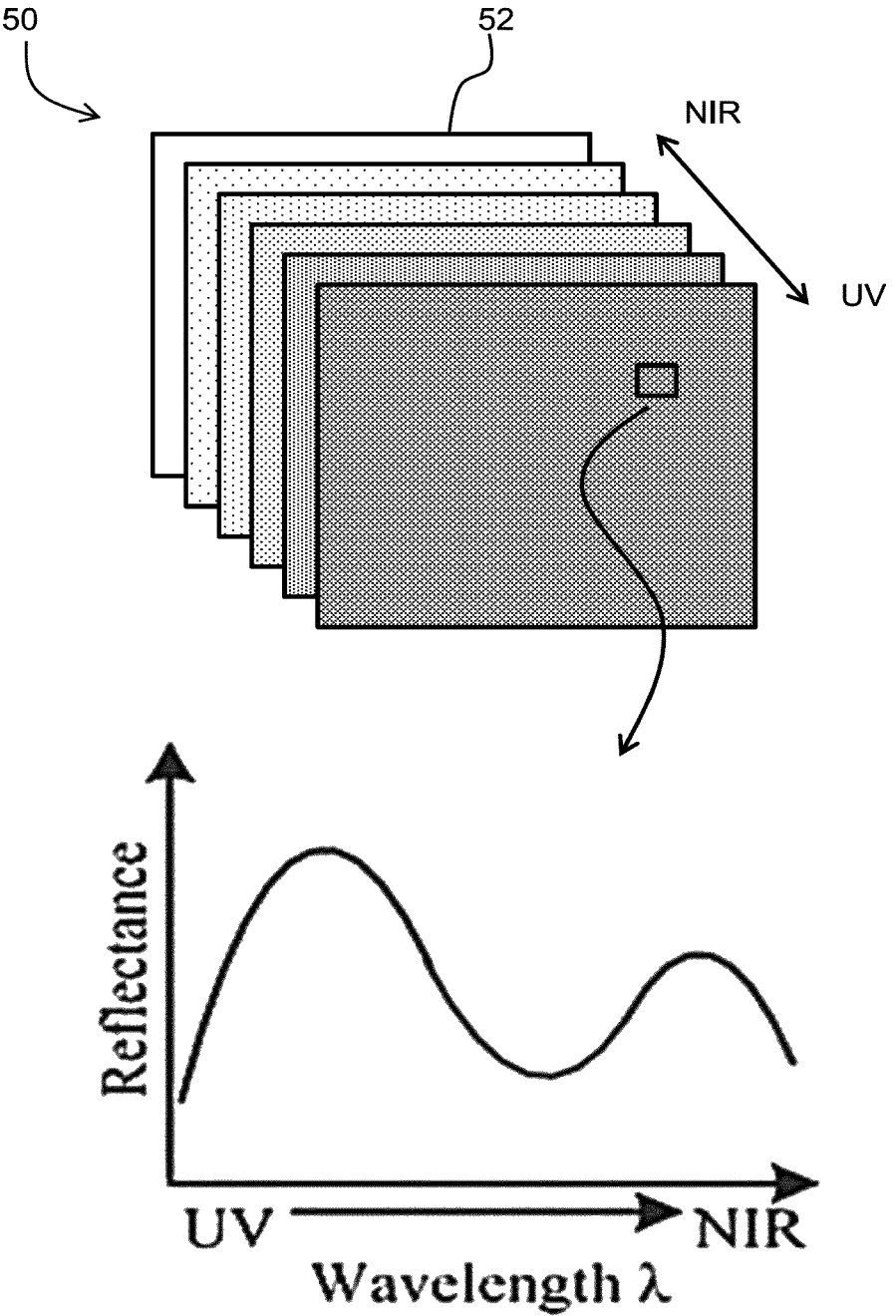
FIG. 13 shows a hypercube of a hyperspectral camera.

As shown in FIG. 13, the hypercube is three-dimensional dataset 50 comprising two-dimensional images 52 at each of a set of wavelengths. FIG. 13 also shows a reflectance curve (i.e. the spectral signature) of a pixel in each image.

The use of hyperspectral images allows additional image processing to be performed, for example it enables a level of oxygenation of tissue to be obtained. A contact PPG probe contains two LEDs and photodetectors at two different wavelengths. By combining the readings at these two wavelengths, an estimation of the oxygen level is possible. For non-contact PPG, RGB cameras have red, green, and blue channels but they are sensitive to much broader wavelength ranges, so extracting oxygenation from a normal RGB camera is not possible. The HSI camera acquires images at specific and narrow wavelengths, so the images can be combined to extract oxygenation values.

The imaging sensor or camero 112 of the system may for example comprise a charged coupled device (CCD) to record images and output the images in analog or digital electronic format or signal. The imaging sensor can comprise or be a camera. Such imaging sensors or cameras are known in the art and available from several vendors.

The system, processor or processor circuit may have an input interface 200 communicatively coupled to the processor, or processor circuit where the input interface is configured to receive images 96 from the imaging sensors to be used by the processor. For example, the images may be received in the analog or digital electronic format or signal.

Functions and methods relating to image processing, data processing and/or output or image generation for output to a user as described herein can be implemented in a general-purpose computer, a processor, processor circuit. Suitable processors or processor circuits include, by way of example processor 203 comprising one or more of, a general-purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors may be made with semiconductor technology as is known in the art.

The system or processor (processor circuit) preferably includes a memory 204 accessible by the processor.

The system or processor (processor circuit) includes an output interface 208 in communicatively coupled to the processor (processor circuit) and configured to output result data and/or images 210 to a user interface or other device 116 for further processing of the result. Exemplifying user interfaces include a display device having an input for coupling to the output interface and receiving the result data to generate a display of images or the result visible to a user.

Functions and methods related to e.g., image and/or data processing and/or data or image generation described herein can be implemented in a computer program, software, or firmware incorporated in a non-transitory computer-readable storage medium and/or downloadable from a communications network for execution by a general-purpose computer, processor or processor circuit.

A computer program 206, software or firmware may thus be stored/distributed on a suitable medium an optical storage medium or a solid-state medium supplied together with or as part of other hardware. Examples of non-transitory computer-readable storage media include a read only memory (ROM), such as electrically programmable ROM (EPROM), electrically erasable programmable ROM (EEPROM or a random access memory (RAM) such as Dynamic RAM (DRAM) or static RAM (SRAM), a register, cache memory, semiconductor memory devices, magnetic media such as internal hard disks and removable disks, magnetooptical media, and optical media such as CD-ROM disks, and digital versatile disks (DVDs). The medium may be a memory of the system accessible by the processor or processor circuit of the system.

Alternatively, or additionally a computer program, software or firmware may be stored and distributed and downloadable from communications network such as wide area network (WAN), local area network (LAN) or Wireless LAN (WLAN), such as the Internet or via other wired or wireless telecommunication systems such as for example 3G, 4G, or 5G networks. If the term "adapted to" is used in the claims or description, it is noted the term "adapted to" is intended to be equivalent to the term "configured to". If the term "arrangement" is used in the claims or description, it is noted the term "arrangement" is intended to be equivalent to the term "system", and vice versa.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

Any reference signs in the claims should not be construed as limiting the scope.

The invention claimed is:

1. A system for tissue analysis, comprising:
an image sensor configured to capture images of tissue; and
a processor adapted to receive images captured by the image sensor and to process the images to:
derive a photoplethysmography (PPG) perfusion map from PPG amplitude levels obtained from the images;
derive a PPG delay map from PPG relative delays between different image regions, wherein the relative delays comprise a delay relative to a reference PPG signal which is an average delay time period for all image regions for a frame of image data;
segment the images into one or more tissue regions based on the PPG delay map or receive segmentation information identifying tissue regions derived from the PPG delay map, wherein the different tissue regions have distinct PPG delay characteristics; and
determine a level of perfusion separately for each tissue region.

2. The system of claim 1, wherein the processor is adapted to segment the images based on regions with distinct ranges of PPG delay.

3. The system of claim 2, wherein the processor is adapted to segment the images using a machine learning algorithm.

4. The system of claim 1, wherein the processor is adapted to control a display to display the PPG perfusion map and the PPG delay map, and receive the segmentation information from a user to whom the PPG perfusion map and PPG delay map have been displayed.

5. The system of claim 1, wherein the processor is adapted to normalize the level of perfusion for each tissue region relative to a maximum level of perfusion within each tissue region.

6. The system of claim 1, wherein the reference PPG signal is an average PPG signal for a global region of interest including all of the tissue regions.

7. The system of claim 1, wherein the tissue regions comprise tissue regions supplied by different arterial branches.

8. The system of claim 1, further comprising an image sensor for capturing the images.

9. A computer-implemented tissue analysis method, comprising:
receiving image sensor images;
deriving a photoplethysmography (PPG) perfusion map from PPG amplitude levels obtained from the images;

deriving a PPG delay map from PPG relative delays between PPG signals of each image region with respect to a reference signal, wherein the relative delays comprise a delay relative to a reference PPG signal which is an average delay time period for all image regions for a frame of image data;
segmenting the images into one or more tissue regions based on the PPG delay map or receiving segmentation information identifying tissue regions derived from the PPG delay map, wherein the different tissue regions have distinct PPG delay characteristics; and
determining a level of perfusion separately for each tissue region.

10. The method of claim 9, comprising segmenting the images based on regions with distinct range of PPG delay.

11. The method of claim 9, comprising normalizing the level of perfusion for each tissue region relative to a maximum level of perfusion within each tissue region.

12. The method of claim 9, wherein said relative delays comprise a delay relative to a reference PPG signal which is a spatial average of all the image regions in the image sensor image.

13. A non-transitory computer-readable storage medium having stored a computer program comprising instructions to perform a method comprising:
receiving image sensor images;
deriving a photoplethysmography (PPG) perfusion map from PPG amplitude levels obtained from the images;
deriving a PPG delay map from PPG relative delays between PPG signals of each image region with respect to a reference signal, wherein the relative delays comprise a delay relative to a reference PPG signal which is an average delay time period for all image regions for a frame of image data;
segmenting the images into one or more tissue regions based on the PPG delay map or receiving segmentation information identifying tissue regions derived from the PPG delay map, wherein the different tissue regions have distinct PPG delay characteristics; and
determining a level of perfusion separately for each tissue region.

14. A processor configured to:
derive a photoplethysmography (PPG) perfusion map from PPG amplitude levels obtained from the images;
derive a PPG delay map from PPG relative delays between different image regions, wherein the relative delays comprise a delay relative to a reference PPG signal which is an average delay time period for all image regions for a frame of image data;
segment the images into one or more tissue regions based on the PPG delay map or receive segmentation information identifying tissue regions derived from the PPG delay map, wherein the different tissue regions have distinct PPG delay characteristics; and
determine a level of perfusion separately for each tissue region.

* * * * *